United States Patent [19]

Matsuyama et al.

[11] 4,045,463

[45] Aug. 30, 1977

[54] PEROXYESTERS OF SORBIC ACID

[75] Inventors: Kazuo Matsuyama, Gamagori; Takeshi Komai, Aichi, both of Japan

[73] Assignee: Nippon Oil and Fats Co., Ltd., Tokyo, Japan

[21] Appl. No.: 671,553

[22] Filed: Mar. 29, 1976

[30] Foreign Application Priority Data

Apr. 4, 1975 Japan .................................. 50-40372
June 7, 1975 Japan .................................. 50-68971

[51] Int. Cl.$^2$ ........................................... C07C 179/18
[52] U.S. Cl. .............................. 260/453 RZ; 260/861; 526/227
[58] Field of Search ................................ 260/453 RZ

[56] References Cited

U.S. PATENT DOCUMENTS 3,408,423  10/1968  Friedman et al. ............... 260/453 R
3,536,676  10/1970  Mageli et al. ................... 260/453 R

FOREIGN PATENT DOCUMENTS 1,041,088  9/1964  United Kingdom ........... 260/453 R

OTHER PUBLICATIONS

J. Amer. Chem. Soc., vol. 89, pp. 3777–3782, (1967).
Derwent Abst., vol. 2, No. 19, pp. 5972.

*Primary Examiner*—Delbert R. Phillips
*Attorney, Agent, or Firm*—Blanchard, Flynn, Thiel, Boutell & Tanis

[57] ABSTRACT

Stable peroxyesters containing both conjugated diene and peroxidic groups in their molecule; e.g., t-butylperoxysorbate, t-hexylperoxysorbate, 1,1,3,3-tetramethylbutylperoxysorbate, are copolymerizable with other polymerizable monomers and the said compounds are useful for polymerizing monomers as free radical initiators.

7 Claims, No Drawings

PEROXYESTERS OF SORBIC ACID

BACKGROUND OF THE INVENTION

1. Field of the Invention

This invention relates to t-alkylperoxysorbates having both conjugated diene and peroxidic groups in their molecule and to their use as free radical initiators in the formation of polymers and as comonomers in the formation of copolymers containing pendant peroxyesters.

2. Description of the Prior Art

Heretofore, there have been known some peroxides having a copolymerizable double bond. For example British Pat. No. 1041 088 discloses that t-butylperoxy methacrylate and methyl methacrylate are copolymerized whereby a copolymer having a peroxyester group is obtained and that the said copolymer is subjected to a graft copolymerization.

U.S. Pat. No. 3536,676 discloses that di (t-butylperoxy) fumarate and styrene are copolymerised whereby there is obtained a copolymer having a peroxyester group and the said copolymer and methyl acrylate are subjected to graft copolymerization.

Japanese Patent Publication SHO 38-5972 discloses that t-butylperoxycrotonate and vinyl chloride are copolymerised to thereby obtain a copolymer having a peroxyester group and the thus obtained copolymer and natural rubber latex are mixed at high temperature whereby blended polymers are obtained.

U.S. Pat. No. 3408, 243 discloses that unsaturated polyester resins are cured at high temperature by using a curing catalyst whereby resins which are splendid in color and hardness are obtained.

The before mentioned compounds locate the peroxyester group and the double bond thereof in the α — and β — positions in their formula. However Japanese Patent Publication SHO 44-21721 discloses that t-butylperoxy vinyl acetate locates them in the β — and γ — positions in the formula and resins which possess good extrusion properties and transparency are obtained by polymerizing ethylene using the said peroxide.

As mentioned above, the peroxyesters having a polymerizable double bond are superior to the peroxyesters not containing a double bond in many points but the former peroxyesters also have some defects in them.

For example such compounds which self polymerize easily such as t-butylperoxy methacrylate as well as the acid chloride thereof which is the starting material therefor, are not stable while being stored and are inconvenient for handling.

Further, a compound which possesses high copolymerization reactivity such as di(t-butylperoxy) fumarate can not distribute the peroxyester group in the polymer uniformly in a broad range of the concentration thereof. Especially, when the concentration of the peroxyester is small, the peroxyester do not give a good copolymer. T-butylperoxy crotonate is small in copolymerisation reactivity with a conjugated monomer having an Aklfrey-Price value of more than 0.3, such as styrene, and as a result it is not suitable for copolymerisation with the monomer. Further, t-butylperoxy vinyl acetate is bad in heat stability and is unsuitable as a copolymerizable monomer.

As mentioned above, there have been disclosed peroxyesters having polymerizable double bonds but peroxyesters having conjugated diene group have not been described heretofore.

SUMMARY OF THE INVENTION

It is an object of the present invention to provide new peroxyesters.

It is another object of the present invention to provide a process for producing new peroxyesters.

It is still another object of the present invention to provide peroxyesters useful as a polymerization initiator.

It is a further object of the present invention to provide a copolymer having peroxyester groups and made by copolymerization of peroxyesters with other monomers. It is still a further object of the present invention to provide peroxyesters useful as a curing agent for resins.

The peroxyesters of the present invention has the following general formula.

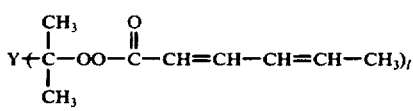

In which *l* is one or two, wherein when *l* is one Y represents an alkyl group of one to twelve carbon atoms or a cycloalkyl group of three to twelve carbon atoms, and when *l* is two, Y represents the group "— C = C — " or the group " — (CH$_2$)m — " wherein *m* is an integer of two to four.

Illustrative peroxyesters are t-butylperoxysorbate, t-hexylperoxysorbate, 1,1,3,3-tetramethylbutylperoxysorbate, 2,5-dimethyl-2,5-di(sorboylperoxy) hexane, 2,5-dimethyl-2,5-di (sorboylperoxy) hexene, p-menthaneperoxysorbate and the like.

These compounds have low self polymerisation reactivity and are good in stability during storage. The peroxyesters of the present invention are obtained by a process similar to that for obtaining common peroxyesters.

These peroxyesters are produced by reacting sorboyl halide with tertiary-alkylhydroperoxide in the presence of an alkali or tertiary amine. One embodiment of the process for producing peroxyesters according to the present invention will be hereinafter described. Tertiary-alkylhydroperoxide is gradually added to an aqueous alkaline solution to form an alkaline metal salt thereof. To the resultant aqueous solution, about one chemical equivalent of sorboyl halide is gradually added. The mixed solution is stirred for a short period. Then, the organic layer containing the peroxyester produced is separated from the aqueous layer. This organic layer is washed with an aqueous solution of sodium hydroxide, sodium bicarbonate, or hot water to remove impurities contained therein thereby obtaining the refined peroxyester.

If the above reaction is carried out in the presence of an organic solvent soluble in water in any ratio and inactive against the reaction, the yield and purity of the peroxyester can be greatly improved.

The temperature of addition and reaction range from −30° C to +40° C, preferably from −10° C to +30° C.

The aqueous alkaline solutions that may be used in this invention include aqueous solutions of the sodium, potassium and barium hydroperoxides. In addition, the above mentioned hydroperoxide may be made to react with sorbic acid in a non-aqueous system using tertiary organic amines such as trimethylamine, triethylamine, pyridine or a non-acrylated heterocyclic base.

The tertiary-alkylhydroperoxide, includes, for example, t-hexylhydroperoxide; 1,1,3,3-tetramethylhydroperoxide; 2,5-dimethylhexane-2,5-dihydroperoxide; 2,5-dimethylhexene-2,5-dihydroperoxide and p-menthanehydroperoxide.

The solvents that may be used in this invention include oil-soluble solvents such as benzene, toluene and alkanes and water-soluble solvents such as dioxane and ethylene glycol.

The infrared absorption spectrum of the peroxyester according to the present invention shows the characteristic absorption of the peroxycarbonyl group occurs at 1764 cm$^{-1}$ ($\nu_{c=o}$), and that of the sorboyl group occurs at 1645 cm$^{-1}$($\nu_{c=c}$), 1618 cm$^{-1}$($\nu_{c=c}$) and 999 cm$^{-1}$ ($\delta$cH). From this result, it is confirmed that the peroxyester of the present invention is a peroxysorbate. Its purity can be determined from the quantity of active oxygen.

POLYMERIZATION AND COPOLYMERIZATION

The peroxyester according to the present invention is useful as an initiator for vinyl polymerization at medium and high temperatures, if it is used under the condition where the peroxy bonds may be broken; and shows an activity higher than t-butylperoxycrotonate, a conventional polymerization initiator. In other words, the peroxyester according to the present invention initiates polymerization earlier than t-butylperoxycrotonate. Furthermore, the peroxyester of the present invention has copolymerizable conjugated double bonds in its molecule, and therefore the obtained polymer is soluble in the solvent, has a high molecular weight and is excellent in transparency though it is a graft polymer. The polymerization temperature may range from about 30° C to 200° C, preferably from 70° C to 150° C. The amount of the peroxyester to be used for polymerization may range from about 0.005 to 1% by weight, preferably 0.01 to 0.5% by weight with respect to the monomers.

In addition, the peroxyester according to the present invention also functions as a copolymerizable monomer, and therefore it can provide a copolymer having peroxyester groups if it is copolymerized with other polymerizable monomers under the conditions where the peroxy double bonds are not broken.

In copolymerization, the relative quantities of peroxyester monomers and other copolymerizable monomers are determined according to the amount of active oxygen desired for the copolymer to be obtained. The amount of active oxygen is influenced by the temperature and the time of copolymerization, and therefore it is desirable to carry out the copolymerization reaction under the conditions where the peroxy bonds are not broken such as at a copolymerization temperature of 70° C or less, preferably at 10° to 50° C. The free radical polymerization initiators which are able to be effectively used within this range include 2-ethylhexanoylperoxide, acetylcyclohexylsulfonylperoxide, isobutylperoxide, diisopropylperoxydicarbonate, di-2-ethylhexylperoxydicarbonate, t-butylperoxypivalate and persulfates. However, copolymerization can be carried out by a self-initiating process without using these initiators.

When the peroxyester of the present invention is copolymerized with other copolymerizable monomers, various kinds of peroxides are produced depending upon the mode of the bond.

Therefore the obtained copolymer contains peroxy bonds different in the decomposition temperature and, as a result, it has an advantage in that the successive processes of crosslinking, blending or block-graft copolymerization can be carried out at temperatures of two or more stages.

The above-mentioned polymerization and copolymerization using the peroxyester of the present invention as a copolymerizable free radical polymerization initiator as well as the above-mentioned copolymerization using the peroxyester of the present invention as a coppolymerizable monomer can be carried out by any of the vinyl polymerization processes well known at present, that is, any of the bulk polymerization process, solution polymerization process, and aqueous medium polymerization process.

Polymerizable monomers for use in the polymerization and copolymerization of the present invention mean those of all the organic compounds (vinyl monomers) having in their molecule at least one $CH_2=C$- group group and the polymeric organic compounds having ethylene type bonds.

The above-mentioned vinyl monomers include those of ethylene, styrene, α-methylstyrene, dichlorostyrene, vinylnaphthalene, vinylphenol, acrylic acid and α-alkyl-substituted acrylic acid; esters of unsaturated acids such as methyl acrylate, methyl methacrylate, butyl methacrylate and propyl methacrylate; vinylidene halides such as vinylidene chloride, vinylidene bromide and vinylidene fluoride; vinyl esters of inorganic acids such as vinyl chloride and vinyl bromide; vinyl esters of halogen hydracids and hydracid cyanides such as acrylonitrile and methacrylonitrile; vinyl esters of monocarboxylic acids such as vinyl acetate, vinyl chloroacetate, vinyl benzoate, vinyl valerate and vinyl capronate; vinyl esters of poly-carboxylic acids such as divinyl succinate, divinyl adipate, vinyl allyl phthalate, vinyl methallyl pimelate and vinyl methyl glutarate; vinyl esters of unsaturated acids such as vinyl acrylate, vinyl crotonate and vinyl methacrylate; vinyl ethers such as vinyl ethyl ether, vinyl butyl ether and vinyl allyl ether; vinyl ketones such as vinyl butyl ketone and vinyl ethyl ketone; allyl derivatives such as allyl acetate, allyl butyrate, diallyl phthalate, diallyl adipate, methallyl propionate, allyl chloride, methallyl chloride, allyl acrylate and methallyl methacrylate; and conjugated dienes such as butadiene and chloroprene.

The above-mentioned polymerizable organic compounds having ethylene type bonds include saturated esters of saturated acids such as diethyl maleate and dibutyl crotonate.

CURING OF UNSATURATED POLYESTER RESIN

The peroxyester of the present invention is more active than t-butylperoxycrotonate in curing unsaturated polyester resins at a suitable temperature under the existence of free radical curing catalyst (makes it cure in a shorter time).

The unsaturated resin which can be cured by the peroxyester of the present invention commonly consists of unsaturated polyester resin and polymerizable monomer.

Unsaturated polyester resins can be obtained by esterifying one or more of polybasic carboxylic acids or anhydrides thereof such as maleic acid, fumaric acid, glutaconic acid, itaconic acid, methaconic acid, citraconic acid, allyl malonic acids and allyl succinic acid with saturated-or unsaturated polyalcohols such as ethylenglycol, diethyleneglycol, triethyleneglycol, 1,2-propanediol, 1,3-propanediol, 1,2-butanediol, 1,4-butanediol, 2,2-dimethyl-1,3-propanediol, 2-butene-1,4-diol, 2-butyne-1,4-diol, glycerin, 2,2,4-trimethyl-1,3-pentanediol, 2,2,4,4-tetramethyl-1,3-cyclobutanediol, 1,4-di(hydroxymethyl)cyclohexane, 1,2,5-hexanetriol, pentaerythritol, and mannitol.

A mixture of the thus mentioned acids and / or a mixture of the thus mentioned alcohols are available for producing the polyester resin.

Unsaturated di - or poly - carboxylic acids may be at least partially substituted with a saturated carboxylic acids such as adipic acid, succinic acid, sebacic acid, or an unsaturated carboxylic acid such as phthalic acid, tetrahydrophthalic acid or anhydride thereof (for example phthalic acid anhydride).

The acids and alcohols may be substituted with halogen or other substituents, preferably with halogen. Such halogen substituted acids include, for example tetrachlorophthalic acid, 1,4,5,6,7,7-hexachloro-2, 3-dicarboxybicyclo (2,2,1)-5-heptane or anhydride of them.

Regarding other components of the unsaturated polyester resin composition, ethylenically unsaturated monomers which are copolymerizable with an unsaturated polyester, such as preferably styrene, chlorostyrene, vinyltoluene, methyl methacrylate, diallyl phthalate, dibutyl fumarate, acrylonitrile, triallyl cyanurate α-methylstyrene, divinylbenzene, ethyl methacrylate ethyl acrylate and the like are mentioned.

The preferred polyester component is an ester of propyleneglycol (polyalcohol), maleic anhydride (anhydride of unsaturated dicarboxylic acid) or phthalic anhydride (anhydride of aromatic carboxylic acid), and styrene as the monomer component.

The curing temperature may range from about 20° C to 200° C, preferably 50° C to 200° C. The amount of the peroxyester of the invention for curing may range about 0.05 to 5.0% by weight (preferably 0.2 to 2.5%) with respect to the curable unsaturated polyester.

PREFERRED EMBODIMENTS OF THE INVENTION

EXAMPLE 1 Production of t-butylperoxysorbate 17.2 g (0.4 mole) of sodium hydroxide was dissolved in 68.8g of water to form a 18.6% aqueous solution of sodium hydroxide, into which 44.3 g (0.4 mole) of t-butylhydroperoxide was added little by little at a temperature of 20° C or less with stirring. To the resultant solution, 26.4 g (0.3 mole) of 1,4-dioxane was added, and then 52.2 g (0.4 mole) of sorboyl chloride was added little by little at 0° C for about 30 minutes.

After the adding operations were completed, the resultant solution were allowed to continue reaction, with stirring, for 2 hours with the temperature kept at 0° C until the reaction was completed. After the aqueous layer was separated, the organic layer was washed twice using 40 ml of an aqueous solution of 5% sodium bicarbonate containing 5 % sodium sulfate, and then was further washed three times using 40 ml of 10% aqueous solution of sodium sulfate, and then was dried using 5 g of magnesium sulfate to obtain 64.2 g of raw product. The amount of active oxygen was 8.14% (theoretical value : 8.68%) and the foaming decomposition temperature was 105° C. This raw product was re-crystallized using acetone to obtain refined crystals of t-butylperoxysorbate with a melting point of 22° C at a yield of 74% (The amount of active oxygen: 8.71%).

The characteristic absorption in the infrared absorption spectrum of this compound occurred at 1764 cm$^{-1}$ ($\nu$ c=o), 1645 cm$^{-1}$ ($\nu$c=c), 1618 cm$^{-1}$ (c=c) and 999 cm$^{-1}$ ($\nu$cH).

EXAMPLE 2

Production of t-hexylperoxysorbate 36.g(0.84 mole) of sodium hydroxide were dissolved into 325 g of water to form a 9.0 wt % aqueous solution of sodium hydroxide, into which 128g of t-hexylhydroperoxide were added. Into the resultant solution 92 g of sorboyl chloride were added little by little at 0° C for 30 minutes with stirring.

After the adding operations were completed, the resultant solution were allowed to continue reaction for two hours with the temperature kept at 0° C. until the reaction was complete.

After the aqueous layer was separated, the organic layer was washed with 5 wt % aqueous solution of sodium bicarbonate and then 10 wt % of aqueous solution of sodium sulphate and then was dried using 10 g of magnesium sulphate to obtain 151 g of t-hexylperoxysorbate.

The amount of active oxygen was 7.61 % (theoretical value : 7.54% ) The foaming decomposition temperature of the product was 105° C.

The characteristic absorption in the infrared absorption spectrum of the compound occurred at 1764 cm$^{-1}$ ($\nu$ c=o), 1645 cm$^{-1}$ ($\nu$ c=c) 1618 cm$^{-1}$ ($\nu$c=c) and 999 cm$^{-1}$ ($\delta$cH).

EXAMPLE 3

Production of 1, 1, 3, 3 - tetramethylbutyl peroxysorbate

Into 9 wt % aqueous solution of sodium hydroxide obtained by dissolving 18 grams (0.4 mole) of sodium hydroxide into 163 grams of water, 73 grams of 1, 1, 3, 3 - tetramethylbutyl hydroperoxide were added.

While being stirred and during a period of 30 minutes 46 grams (0.35 mole) of sorboyl chloride diluted with 90 grams of petroleum ether were dropped into it little by little.

Further after the reaction was continued at 0° C for 2 hours, the organic layer of the resultant product was washed by 5 wt % aqueous solution of bicarbonate and then by water. Following this procedure, after said organic layer was dried by magnesium sulphate, the solvent was removed from it, to thereby obtain 38 grams of 1,1,3,3-tetramethylbutyl peroxysorbate. The content of active oxygen of the obtained product was 6.51% (theoretical value: 6.68 %) and when it was heated, the decomposition temperature thereof was 90° C.

The characteristic absorptions of the infrared absorption spectrum of the product were observed at 1764 cm$^{-1}$ ($\nu$c=o), 1645 cm$^{-1}$ ($\nu$c=c) 1618 cm$^{-1}$ ($\nu$c=c) and 999 cm$^{-1}$ ($\delta$cH).

EXAMPLE 4

Production of 2,5-dimethyl-2,5-di(sorboyl peroxy) hexane.

67 grams (0.35 mole) of 2.5 - dimethylhexane - 2.5-dihydroperoxide were added into 25% by weight in aqueous solution of sodium hydroxide which was obtained by dissolving 30 grams (0.7 mole) of sodium hydroxide into 121 grams of water. Into the resultant solution, 100 grams (0.77 mole) of sorboyl chloride which was diluted with 100 grams of petroleum ether were dropped at 5° C during 1.5 hours and further 0.5 g of anionic surfactant (tracks K) was added into it. After the resulting mixture was reacted at 5° C for another 2 hours, the same quantity of ether as that of the resultant product was added thereto.

Then the resultant product was washed by 5 wt % aqueous solution of sodium bicarbonate and by water. After this procedure, the resultant product was dried by magnesium sulphate and the solvent was distilled off under reduced pressure. The thus obtained product was recrystallized in acetone, whereby 45 grams of 2.5 -dimethyl - 2.5 di(sorboylperoxy) hexane were obtained. The melting point of the compound was 105° C (decomposition) and the content of the active oxygen was 8.11% (theoretical value 8.73%).

The decomposition temperature thereof was 105 - 106° C. The characteristic absorptions of the infrared absorption spectrum of this compound were observed at 1764 cm$^{-1}$ ($vc=o$), 1645 cm$^{-1}$ ($vc=c$), 1618 cm$^{-1}$ ($vc=c$) and 999 cm$^{-1}$ ($\delta cH$).

EXAMPLE 5 Half-life period of polymerization initiator

The half-life periods of the polymerization initiators according to the present invention were measured in cumene at 100° C. In addition, the half-life period of t-butylperoxycrotonate widely used for medium and high temperature polymerizations was measured under the same conditions.

The results are shown in Table 1. It is understood from this table that the polymerization initiator of the present invention is active at a lower temperature than t-butylperoxycronate usually used at present.

As shown in Table 1, t-butylperoxyvinylacetate (disclosed in Japanese Patent Publication No. 21721/69) is active at low temperatures, it is not suitable for copolymerizable monomers because it decomposes under the copolymerization conditions.

Table 1.

| Half-life periods in cumene at 100° C | |
|---|---|
| Polymerization initiator | Half-life period (Hours) |
| t-butylperoxysorbate | 6.5 |
| t-hexylperoxysorbate | 6.4 |
| 1.1.3.3-tetramethylbutylperoxysorbate | 2.3 |
| 2,5-dimethyl-2,5-di(sorboylperoxy)-hexane | 3.3 |
| t-butylperoxycrotonate | 12.8 |
| t-butylperoxyvinylacetate *[1] | 0.017 |

*[1] is cited from the data mentioned in the Japanese Patent Publication No. 21721/69.

EXAMPLE 6

Polymerization of styrene 15 ml of 0.09 mol/l styrene solution of the respective polymerization initiators as shown in Table 2 were placed in ampoules.

After the atmosphere in the respective ampoules was substituted with nitrogen gas by cooling and melting method, bulk polymerization of styrene was carried out at 100° C.

After the polymerization reaction was over, the obtained polymers was cooled and dissolved in benzene and then precipitated by pouring twenty times of volume of methyl alcohol as that of the polymer into the resultant solution of the polymer. The polymers were filtered off and dried and weighed to calculate the polymerization rate thereof.

Further the intrinsic viscosity of the polymer in toluene at 30° C was measured.

The obtained results and the solubility of the polymer are shown in Table 2.

Table 2.

| Bulk polymerization of styrene at 100° C. | | | |
|---|---|---|---|
| Polymerization Initiator | | Polymerization Period (hour) | |
| | | 2.0 | 6.0 |
| t-butyl peroxysorbate | rate of polymerization (%) | 89.6 | 98.1 |
| | intrinsic viscosity | 0.487 | 0.721 |
| | solubility | soluble | soluble |
| t-butyl peroxy crotonate | rate of polymerization | 88.4 | 96.4 |
| | viscosity | 0.207 | 0.294 |
| | solubility | soluble | soluble |

It will be recognized from Table 2 that t-butyl peroxysorbate is more active than t-butyl peroxycrotonate which is used as a polymerization initiator at high and medium temperature, (in other works, it makes styrene polymerize rapidly) and that when it is used as a polymerization initiator, polystyrene which has a large molecular and weight soluble in a solvent can be obtained.

EXAMPLE 7 - 10

Copolymerization with styrene (free radical initiation method)

Co-polymerization reactions of t-butyl peroxysorbate and styrene in the mole ratio as shown in Table 3 was carried out in 50% solution of benzene at 40° C for 40 hours, using 0.1 % by weight of di-isopropylperoxy dicarbonate based on the styrene as the free radical polymerization initiator.

The thus obtained respective copolymers were precipitated with 10 times quantity of methanol based on the copolymers as a precipitant and were filtered off and were dried and weighed, whereby the copolymerization rate thereof was measured. Further the intrinsic viscosity and the content of the active oxygen of the obtained respective-copolymers were measured.

The obtained results are shown in Table 3.

Table 3.

| Copolymerization of t-butylperoxy sorbate with styrene at 40° C for 40 hours | | | | |
|---|---|---|---|---|
| Examples | 7 | 8 | 9 | 10 |
| mole rate of t-butyl peroxysorbate to styrene | 0.102 | 0.225 | 0.387 | 0.622 |
| Polymerization rate (%) | 53.6 | 42.0 | 24.7 | 11.6 |
| Intrinsic viscosity[2] | 0.080 | 0.053 | 0.043 | 0.044 |
| Content of active oxygen | 0.266 | 0.569 | 0.609 | 0.984 |

[2] Intrinsic viscosity of the copolymer was measured in benzene at 30° C.

It will be recognized that the thus obtained copolymer is a copolymer of tert-butylperoxy-sorbate with styrene because the copolymer has active oxygen, and in the IR spectra thereof, the peak which are the characteristics of mono-substituted benzene at 1800 - 2000 cm$^{-1}$, the broader peak of carbonyl groups of two or more kinds of peroxyesters at 1762 cm$^{-1}$ and the peak of the double bond conjugated with the carbonyl radical are observed.

It will also be understood that the copolymer has two or more kinds of peroxides in the molecule, because the differential thermoanalysis thereof showed the existence of exothermic peaks at 80° - 90° C and 125° - 145° C.

According to these results, it will be understood that polymerization ability of t-butylperoxysorbate with styrene is large and that as the mixing ratio of t-butylperoxysorbate in the resultant mixture of the two monomers is increased, the content of the active oxygen of the obtained copolymer is increased and is dispersed uniformly therein.

EXAMPLE 8

Copolymerization with styrene (self-initiating method)

Without employing diisopropylperoxydicarbonate, a mixture of styrene and 0.217 mol % of t-butylperoxy sorbate based on the styrene was subjected to copolymerization for 36 hours, according to the method described in Example 4 - 7.

Polymerization rate of the thus obtained copolymer was 43.8%, the intrinsic viscosity thereof was 0.058 and the content of active oxygen was 0.664.

It will be recognized from these results that the compound of the present invention may copolymerize with a copolymerizable monomer without using a free radical initiator.

EXAMPLE 9

Curing of an unsaturated polyester resin

According to the testing method of curing at high temperature which is described in Japanese Industrial Standard K - 6901, a curing test was conducted using a commercially available unsaturated polyester resins (made by Nippon Catalytic Chemistry Co. Ltd as trade mark of Eporack G - 110AL)

The amount used of the catalyst was made equivalent to 1 wt % of dibenzoylperoxide in connection with the content of the active oxygen. t-butylperoxysorbate, a compound of the present invention, was evaluated as a curing agent for an unsaturated polyester resin at 100° C by the mentioned process.

The obtained results are shown in Table 4.

Table 4.

| Curing of unsaturated resins at 100° C. | | | |
|---|---|---|---|
| Peroxide | gel time (minutes) | minimum curing time (minutes) | maximum exothermic temperature (° C) |
| t-butylperoxysorbate | 4.2 | 7.5 | 214 |
| t-butylperoxycrotonate | 6.6 | 9.9 | 228 |

These results show that t-butylperoxysorbate is more active for curing resins than t-butylperoxycrotonate.

What is claimed is:

1. A compound having the formula

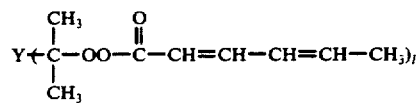

wherein *l* is one or two,
wherein when *l* is one, Y is alkyl having one to twelve carbon atoms or cycloalkyl having three to twelve carbon atoms, and
wherein when *l* is two, Y is —C=C— or —(CH$_2$)$_m$—, wherein *m* is a number of from two to four.

2. A compound as claimed in claim 1, t-butylperoxy sorbate.

3. A compound as claimed in claim 1, t-hexylperoxy sorbate.

4. A compound as claimed in claim 1, 1,1,3,3-tetramethylbutylperoxy sorbate.

5. A compound as claimed in claim 1, 2,5-dimethyl-2,5-di(sorboylperoxy) hexane.

6. A compound as claimed in claim 1, 2,5-dimethyl-2,5-di(sorboylperoxy) hexene.

7. A compound as claimed in claim 1, p-methaneperoxy sorbate.

* * * * *